United States Patent [19]

Müller et al.

[11] Patent Number: 5,300,537
[45] Date of Patent: Apr. 5, 1994

[54] CARBOXAMIDO (METH) ACRYLIC ACID ESTERS FOR TREATMENT OF COLLAGEN

[75] Inventors: Michael Müller, Bergisch-Gladbach; Wolfgang Podszun, Cologne; Bernd Alker, Bergisch-Galdbach, all of Fed. Rep. of Germany

[73] Assignee: Bayer Aktiengesellschaft, Leverkusen, Fed. Rep. of Germany

[21] Appl. No.: 962,994

[22] Filed: Oct. 19, 1992

Related U.S. Application Data

[62] Division of Ser. No. 509,008, Apr. 12, 1990, abandoned.

[30] Foreign Application Priority Data

Apr. 27, 1989 [DE] Fed. Rep. of Germany ....... 3913939

[51] Int. Cl.5 .......................... A61F 2/00; C08K 5/20; A61K 6/00
[52] U.S. Cl. .................................... 523/115; 523/116; 523/118; 526/304; 526/306; 433/228.1
[58] Field of Search .............. 523/116, 118, 120, 112, 523/115; 433/228.1; 526/304, 306

[56] References Cited

U.S. PATENT DOCUMENTS 3,366,613 1/1968 Kelley ................................ 260/89.5
(List continued on next page.)

FOREIGN PATENT DOCUMENTS 0141324 5/1985 European Pat. Off. .
(List continued on next page.)

OTHER PUBLICATIONS

Scand. J. Dent. Res. 92, 480–483 (not 980–983) (1984).
(List continued on next page.)

*Primary Examiner*—Paul R. Michl
*Assistant Examiner*—Tae H. Yoon
*Attorney, Agent, or Firm*—Sprung Horn Kramer & Woods

[57] ABSTRACT

For bonding dental fillings to dentine, carboxamide group-containing (meth)acrylic acid ester of the formula

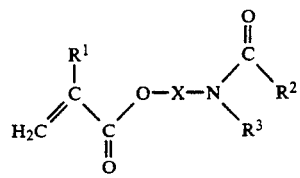

in which
 $R^1$ denotes hydrogen or methyl,
 $R^2$ denotes alkyl ($C_1$–$C_4$) or alkenyl ($C_2$–$C_4$), optionally substituted by hydroxyl, carboxyl, halogen or amino of the formula

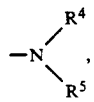

in which
 $R^4$ and $R^5$ are identical or different and denote hydrogen or lower alkyl,
 $R^3$ denotes hydrogen or has one of the abovementioned meanings of $R^2$ and
 X is a divalent aliphatic ($C_1$–$C_6$) or cycloaliphatic radical ($C_3$–$C_6$), which can optionally contain one or more oxygen, sulphur and/or —$NR^4$-bridges,
where
 $R^4$ has the abovementioned meaning.

11 Claims, No Drawings

U.S. PATENT DOCUMENTS

| | | | |
|---|---|---|---|
| 4,039,513 | 8/1977 | Naarmann et al. | 528/246 |
| 4,323,696 | 4/1982 | Schmitz-Josten et al. | 560/220 |
| 4,439,380 | 3/1984 | Michl et al. | 433/228.1 |
| 4,548,689 | 10/1985 | Sakashita et al. | 523/116 |
| 4,593,054 | 6/1986 | Asmussen et al. | 523/118 |
| 4,771,084 | 9/1988 | Kubota et al. | 523/116 |
| 4,910,259 | 3/1990 | Kindt-Larsen et al. | 523/116 |
| 4,952,241 | 8/1990 | Reiners et al. | 106/35 |
| 4,952,614 | 8/1990 | Reiners et al. | 523/115 |

FOREIGN PATENT DOCUMENTS

| | | |
|---|---|---|
| 0264551 | 4/1988 | European Pat. Off. . |
| 0326132 | 8/1989 | European Pat. Off. . |
| 0355562 | 2/1990 | European Pat. Off. . |
| 3703080 | 1/1988 | Fed. Rep. of Germany . |
| 2301539 | 9/1976 | France . |
| 47-36265 | 9/1972 | Japan . |
| 2009745 | 6/1979 | United Kingdom . |

OTHER PUBLICATIONS

Scand. J. Dent. Res. 88, 348–351 (1980).

J. Dent. Res. 63 1087–1089 (1984).

J. Dent. Res. 57, 500–505 (1978).

A. Pleurdeav et al., Eur. Polym. J. 18 (1982) 627.

Houben–Weyl Methoden der organischen Chemie (Methods of Organic Chemistry), vol. E 20, p. 80 et seq., Georg Thieme Verlag, Stuttgart (1987).

R. S. Baratz, Journals of Biomaterials Applications, vol. 1, (1987), p. 316 et seq.

K. Eichner, "Zahnärzliche Werkstoffe und ihre Verarbeitung" (Dental materials and their processing) vol. 2, p. 135 et seq., Hüthig Verlag, 5th Edition (1985).

CARBOXAMIDO (METH) ACRYLIC ACID ESTERS FOR TREATMENT OF COLLAGEN

This application is a division, of application Ser. No. 509,008, filed Apr. 12, 1990 now abandoned.

The invention relates to new carboxamide group-containing (meth)acrylic acid esters (I) and preparations (II), which contain compounds (Ia), for use as an adhesive component for the treatment of collagen-containing materials, and to processes for the preparation and to the use of the preparations (II).

The new carboxamide group-containing (meth)acrylic acid esters correspond to the formula (I)

$$\underset{H_2C}{\overset{R^1}{=}}C\underset{\underset{O}{\parallel}}{\overset{}{-}}C-O-X-N\underset{R^3}{\overset{R^2}{\diagdown}}\overset{O}{\underset{}{\parallel}}C \qquad (I)$$

in which
R$^1$ denotes hydrogen or methyl,
R$^2$ denotes alkyl (C$_1$–C$_4$) or alkenyl (C$_2$–C$_4$), optionally substituted by hydroxyl, carboxyl, halogen or amino of the formula $$-N\overset{R^4}{\underset{R^5}{\diagdown}}$$

in which
R$^4$ and R$^5$ are identical or different and denote hydrogen or lower alkyl,
R$^3$ denotes hydrogen or has one of the abovementioned meanings of R$^2$ and
X is a divalent aliphatic (C$_1$–C$_6$) or cycloaliphatic radical (C$_3$–C$_6$) which can optionally contain one or more oxygen, sulphur and/or —NR$^4$-bridges, where
R$^4$ has the abovementioned meaning, and
which is optionally substituted by hydroxyl, carboxyl, halogen or amino of the formula $$-N\overset{R^4}{\underset{R^5}{\diagdown}}$$

in which R$^4$ and R$^5$ have the abovementioned meaning with the proviso that
a) the sum of the carbon atoms in the radicals R$^2$, R$^3$ and X is not greater than six if these radicals contain no hetero-atoms, or
b) the sum of the carbon atoms in the radicals R$^2$, R$^3$, R$^4$, R$^5$ and X is not greater than ten if at least one of these radicals contains at least one hetero-atom.

The carboxamide group-containing (meth)acrylic acid esters (1) according to the invention can be prepared, for example, by reaction of alkanolamines with carboxylic acid esters and (meth)acryloyl chloride.

Similar processes for the preparation of (meth)acrylic acid ester derivatives are described in JP 47-36,265 (72-36,265).

The invention additionally relates to preparations (II), which contain compounds (Ia), for use as adhesive component for the treatment of collagen-containing materials, to processes for the preparation and to the use of the preparations (II).

The claimed preparations (II) contain carboxamide group-containing (meth)acrylic acid esters (Ia) of the formula $$\underset{H_2C}{\overset{R^1}{=}}C\underset{\underset{O}{\parallel}}{\overset{}{-}}C-O-X-N\underset{R^3}{\overset{R^2}{\diagdown}}\overset{O}{\underset{}{\parallel}}C \qquad (Ia)$$

in which
R$^1$ denotes hydrogen or methyl,
R$^2$ denotes alkyl (C$_1$–C$_4$) or alkenyl (C$_2$–C$_4$), optionally substituted by hydroxyl, carboxyl, halogen or amino of the formula $$-N\overset{R^4}{\underset{R^5}{\diagdown}}$$

in which
R$^4$ and R$^5$ are identical or different and denote hydrogen or lower alkyl,
R$^3$ denotes hydrogen or has one of the abovementioned meanings of R$^2$ and
X is a divalent aliphatic (C$_1$–C$_6$) or cycloaliphatic radical (C$_3$–C$_6$), which can optionally contain one or more oxygen, sulphur and/or —NR$^4$-bridges, where
R$^4$ has the abovementioned meaning,
and which is optionally substituted by hydroxyl, carboxyl, halogen or amino of the formula $$-N\overset{R^4}{\underset{R^5}{\diagdown}}$$

in which R$^4$ and R$^5$ have the abovementioned meaning, with the proviso that
a) the sum of the carbon atoms in the radicals R$^2$, R$^3$ and X is not greater than six if these radicals contain no hetero-atoms, or
b) the sum of the carbon atoms in the radicals R$^2$, R$^3$, R$^4$, R$^5$ and X is not greater than ten if at least one of these radicals contains at least one hetero-atom, and, if appropriate, initiators.

Collagen-containing materials are albuminoid bodies and principal constituents of the human and animal intercellular supporting substances, such as cartilage and bone tissue, skin and dentine. In the context of the present invention, the adhesive components (II) are preferably used for the treatment of dentine in connection with dental repairs.

Particularly in the dental field, setting polymeric materials are used as filling materials in dental repairs. In general, fillings based on acrylates are prefered as setting polymeric materials. However, these polymeric fillings have the disadvantage that they adhere poorly to the dentine. In order to solve this problem, undercuttings to the dental bone have previously sometimes been carried out; for this purpose it was necessary to remove considerable amounts of fresh dentine beyond the affected region.

According to another method, the dentine and the enamel surface are etched with acids, such as, for example, phosphoric acid, and the filling is then performed. Apart from the fact that the acid exerts an irritant action in the oral region, it also penetrates easily into the tooth through the dental tubules and damages the nerve (pulp).

In J. Dent. Res. 57, 500–505 (1978), aldehyde group-containing methacrylates of the isomeric hydroxybenzaldehydes are described which can be used as foundations for fillings in the dental field. However, even after such a foundation, the bond between dentine and filling material remains unsatisfactory.

In Scand. J. Dent. Res. 92, 980–983 (1948) and J. Dent. Res. 63, 1087–1089 (1984), foundations based on aqueous formaldehyde or glutaraldehyde and β-hydroxyethyl methacrylate (HEMA) are described.

In addition, compositions formed from an aldehyde and an olefinically unsaturated monomer containing active hydrogen, which bond well to dentine, are described in EP-A 0,141,324.

The new preparations (II) based on aliphatic carboxamide group-containing (meth)acrylic acid esters (Ia) effect a strong adhesive bonding of materials which are intended to be attached to collagen, for example an adhesive bonding of dental filling material in a cavity in the tooth.

2-Carboxamidoethyl methacrylates are known for the preparation of water-soluble polymers from JP 47/36265 [72/36265]. An aromatic methacrylic acid ester containing an acetamide group was used as a protein model after polymerization (A. Pleurdeav et. al Eur. Polym. J. 18 (1982), 627).

Formamide group-containing (meth)acrylic acid esters are known from DE-A-2,507,189. In DE-A-2,507,189 the use of these acrylic acid esters as coatings or adhesives for paper and textiles is also described.

The use of the carboxamide group-containing (meth)acrylic acid esters (Ia) according to the invention as adhesive component for collagen-containing materials was surprising since they contain no reactive groups which can build up under mild conditions suitable chemical bonds to collagen-containing materials.

(Meth)acrylic acid esters in the context of the present invention are the esters of acrylic acid and of methacrylic acid.

The substituents of the (meth)acrylic acid esters according to the invention in the context of the general formula (I) and (Ia) in general have the following meaning:

Halogen in general denotes fluorine, chlorine, bromine and iodine, preferably fluorine and chlorine.

Lower alkyl ($R^4$ and $R^5$) in the context of the amino groups in general denotes a straight-chain or branched hydrocarbon radical having 1 to 4 carbon atoms. Methyl and ethyl are preferred.

Amino groups which may be mentioned are, for example, amino, dimethylamino, diethylamino and methyl-ethylamino.

Alkyl ($R^2$, $R^3$) in general denotes a saturated, and alkenyl an olefinically unsaturated, straight-chain or branched hydrocarbon radical having 1 (or 2) to 4 carbon atoms. Examples which may be mentioned are the following alkyl radicals and alkenyl radicals: methyl, ethyl, propyl, isopropyl, butyl, isobutyl and propenyl. Methyl and ethyl are particularly preferred.

A divalent aliphatic radical (X) in general denotes a divalent, straight-chain or branched hydrocarbon radical having 1 to 6, preferably 1 to 3, carbon atoms. Examples which may be mentioned are the following divalent aliphatic radicals.

Hexanediyl, pentanediyl, neopentanediyl, butanediyl, dimethylethanediyl, propanediyl, ethanediyl.

Preferred divalent aliphatic radicals are ethanediyl and propanediyl.

A divalent cycloaliphatic radical (X) in general denotes a cyclic hydrocarbon radical having 4 to 6 carbon atoms. Examples which may be mentioned are the following divalent cycloaliphatic radicals: cyclobutanediyl, cyclopentanediyl and cyclohexanediyl.

The divalent aliphatic and cycloaliphatic radicals X can be substituted by hydroxyl, carboxyl, halogen or amino groups. Preferred substituents are hydroxyl, carboxyl, fluorine, chlorine and amino. X can in general be substituted by 1 to 4 radicals.

However, it is also possible that in X the aliphatic radicals are linked by oxygen, sulphur and/or $-NR^4$-bridges (where $R^4$ has the abovementioned meaning). In this case, it is possible that the aliphatic radicals in each case are linked only by oxygen or sulphur or $-NR^4$. However, it is also possible that different bridge members link the aliphatic radicals with one another.

Divalent radicals are preferred in which ethylene radicals are bonded via oxygen bridges.

The following carboxamide group-containing (meth)acrylic acid esters may be mentioned as examples:

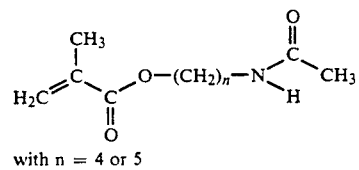

with n = 4 or 5

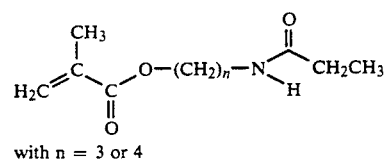

with n = 3 or 4

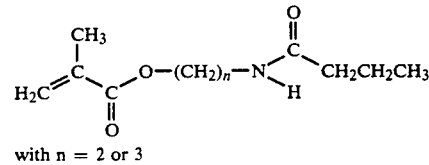

with n = 2 or 3

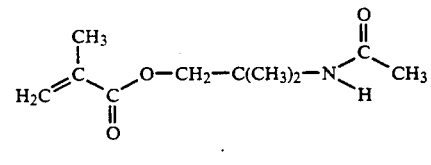

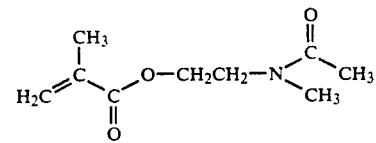

-continued

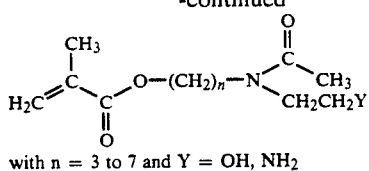

with n = 3 to 7 and Y = OH, NH₂

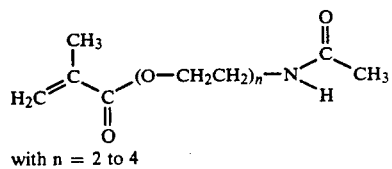

with n = 2 to 4

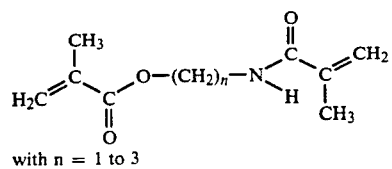

with n = 1 to 3

3-Acetamidopropyl methacrylate and 2-acetamidoethyl methacrylate of the formula

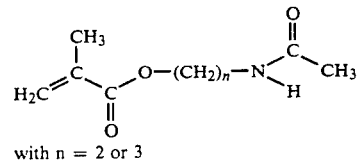

with n = 2 or 3 and 2-(N-2-hydroxyethylacetamido)ethyl methacrylate of the formula

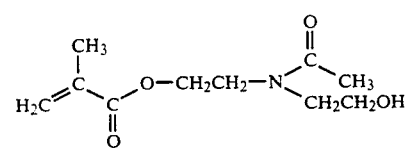

are particularly preferred.

Initiators in the context of the present invention are free radical formers which induce a free radical polymerization. Photoinitiators, which induce a free radical polymerization under the action of light, for example UV light, visible light or laser light, are preferred.

The so-called photopolymerization initiators are known per se (Houben-Weyl, Methoden der organischen Chemie (Methods of Organic Chemistry), Volume E 20, page 80 et seq, Georg Thieme Verlag Stuttgart 1987). Preferably, these are mono- or dicarbonyl compounds, such as benzoin and its derivatives, in particular benzoin methyl ether, benzil and benzil derivatives, for example 4,4-oxydibenzil and other dicarbonyl compounds such as diacetyl, 2,3-pentanedione and a-diketo derivatives of norbornane and substituted norbornanes, metal carbonyls such as magnanese pentacarbonyl or quinones such as 9,10-phenanthrene quinone and naphthoquinone. Camphorquinone is particularly preferred.

The preparations according to the invention in general contain 0.01 to 2 parts by weight, preferably 0.1 to 0.5 parts by weight of the initiator, relative to 1 part by weight of the carboxamide group-containing (meth)acrylic acid ester. If one of the parts to be joined which is in contact with the adhesive component according to the invention already contains an initiator of the type described, the initiator in the adhesive component can even be completely dispensed with.

The solvents in the context of the present invention should dissolve the component and, because of the application, should be non-toxic. Water and volatile organic solvents such as methanol, ethanol, propanol, isopropanol, acetone, methyl ethyl ketone, tetrahydrofuran, methyl acetate or ethyl acetate may be mentioned as preferred.

In general, 10 to 1000 parts by weight, preferably 50 to 300 parts by weight, of the solvent are employed, relative to the carboxamide group-containing (meth)acrylic acid ester.

It may be advantageous to add coactivators, which accelerate the polymerization reaction, to the preparations according to the invention. Known accelerators are, for example, amines such as p-toluidine, dimethyl-p-toluidine, trialkylamines such as trihexylamine, polyamines such as N,N,N',N'-tetraalkylalkylendiamine, barbituric acid and dialkylbarbituric acid.

The coactivators are in general employed in an amount from 0.02 to 4% by weight, preferably 0.2 to 1% by weight, relative to the amount of polymerizable compounds.

The compositions according to the invention may contain carbonyl compounds as a further component.

Carbonyl compounds in the context of the present invention are aldehydes and ketones which contain 1 to 20, preferably 1 to 10, and particularly preferably 2 to 6 carbon atoms. The carbonyl function can be bonded to an aliphatic, aromatic and heterocyclic molecule moiety.

Aldehydes which may be mentioned are aliphatic mono- or dialdehydes. Formaldehyde, acetaldehyde, propionaldehyde, 2-methylpropionaldehyde, butyraldehyde, benzaldehyde, vanillin, furfural, anisaldehyde, salicylaldehyde, glyoxal, glutaraldehyde and phthalaldehyde are preferred. Glutaraldehyde is particularly preferred.

Ketones which may be particularly mentioned are aliphatic mono- and diketones. Butanone, acetone, cyclooctanone, cycloheptanone, cyclohexanone, cyclopentanone, acetophenone, benzophenone, 1-phenyl-2-propanone, 1,3-diphenyl-2-propanone, acetylacetone, 1,2-cyclohexandione, 1,2-cyclopentandione and camphor quinone are preferred. Cyclopentanone is particularly preferred.

In general, 1 to 1000 parts by weight, preferably 5 to 50 parts by weight, of the carbonyl compounds are employed, relative to the carboxamide group-containing (meth)acrylic acid esters.

As further component, the compositions according to the inventions can contain (meth)acrylic acid esters which can form cross-linkages. (Meth)acrylic acid esters which can form cross-linkages in general contain 2 or more polymerizable active groups in the molecule. Esters of (meth)acrylic acid with dihydric to pentahydric alcohols containing 2 to 30 carbon atoms may be mentioned as preferred. Alkoxy(meth)acrylates and urethane group-containing (meth)acrylates are particularly preferred.

(Meth)acrylic acid esters of the formula

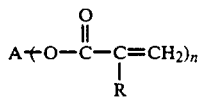

in which

A denotes a straight-chain, branched, cyclic, aliphatic, aromatic or mixed aliphatic-aromatic radical having 2 to 25 C atoms, which can be interrupted by —O—, NH— or O—CO—NH— bridges and can be substituted by hydroxyl, oxy, carboxyl, amino or halogen, R denotes H or methyl and n represents an integer from 2 to 8, preferably 2 to 4, may be mentioned as examples.

Compounds of the following formulae

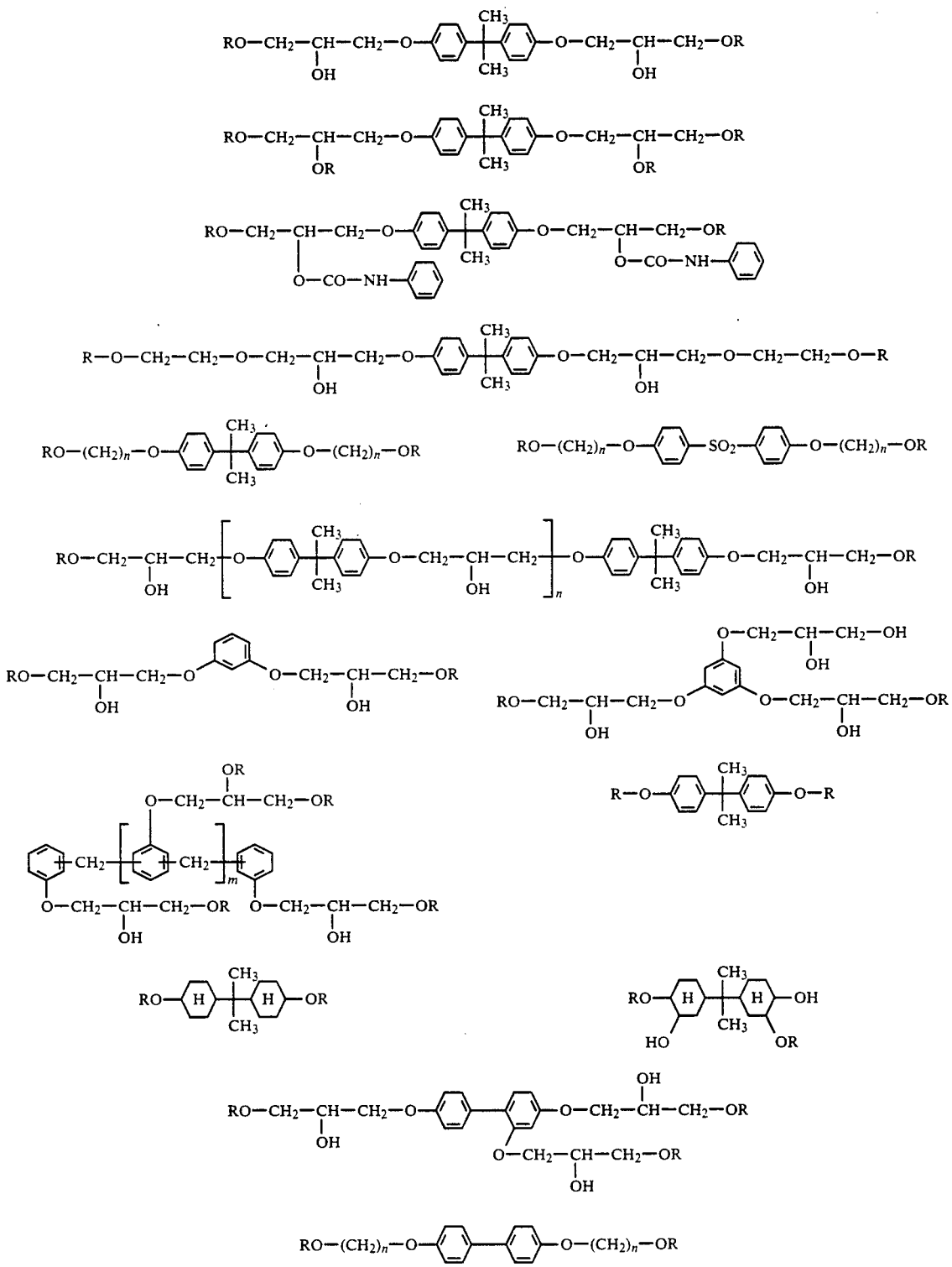

-continued

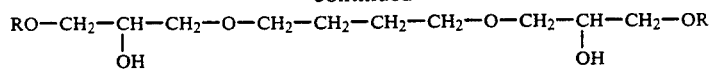
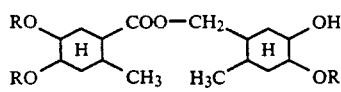 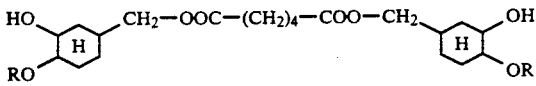
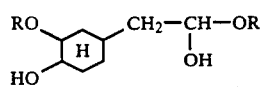 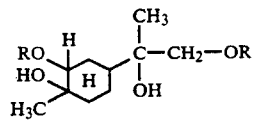
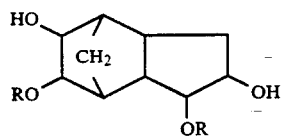
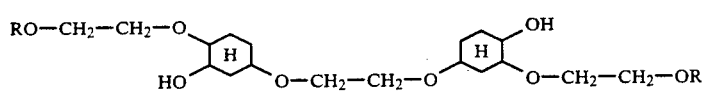
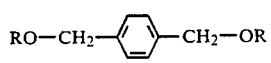 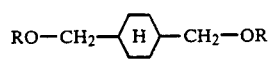
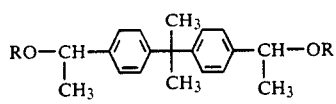 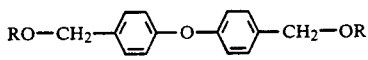

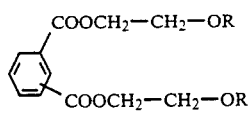

in the ortho-, meta- or para-form

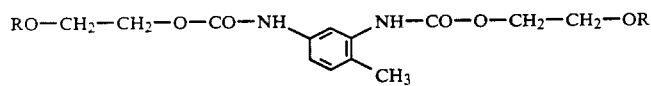
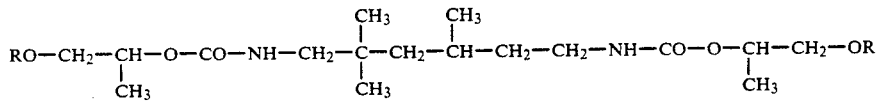
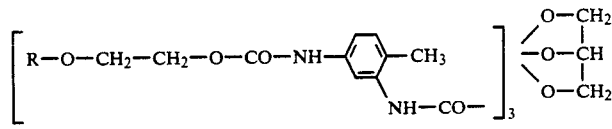
 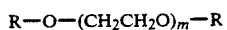
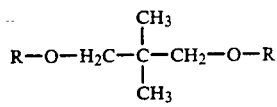

in which
R represents

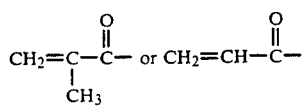

n denotes a number from 1 to 4 and
m denotes a number from 0 to 5,
may be mentioned as preferred.

In addition, derivatives of tricyclodecane (EP-A-0,023,686) and reaction products of polyols, diisocyanates and hydroxyalkyl methacrylates (DE-A-3,703,120, DE-A-3,703,080 and DE-A3,703,130) may be mentioned. The following monomers may be mentioned as examples:

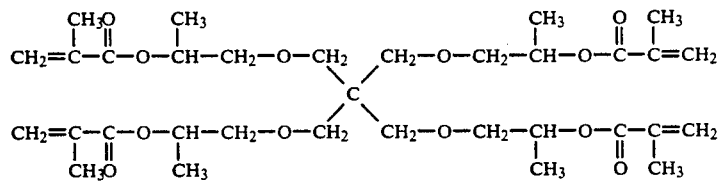
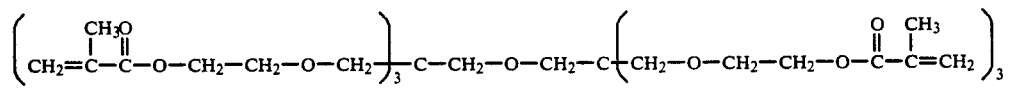
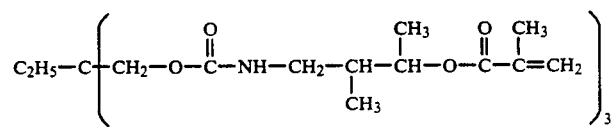
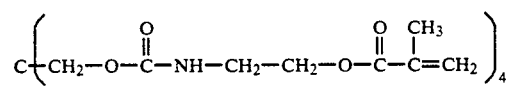
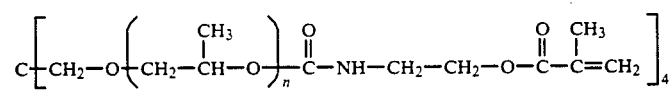
n = 1.225 (statistical mean for 4 chains)
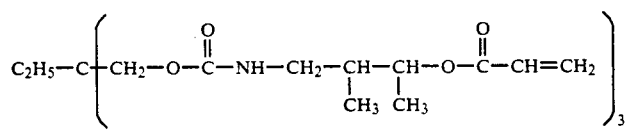
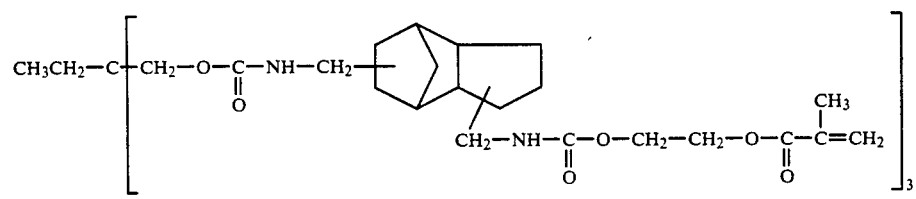
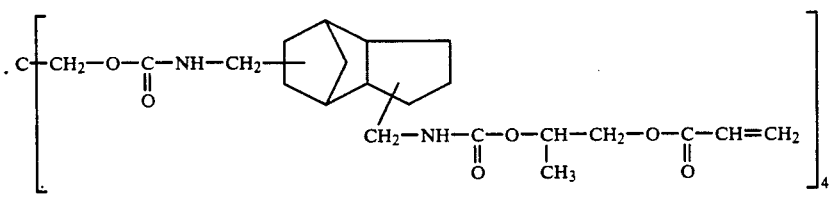
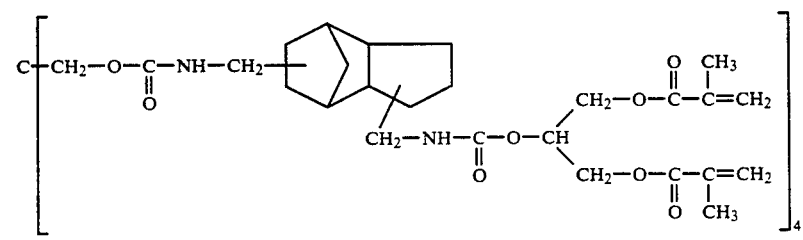

-continued
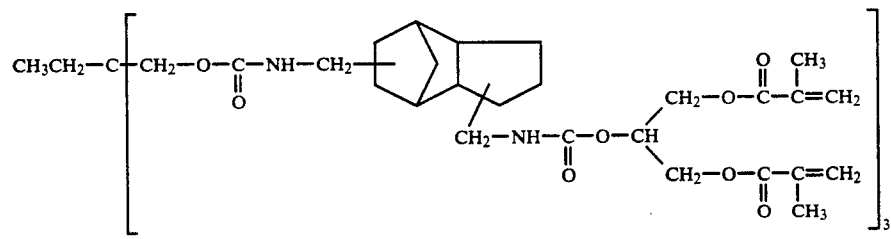
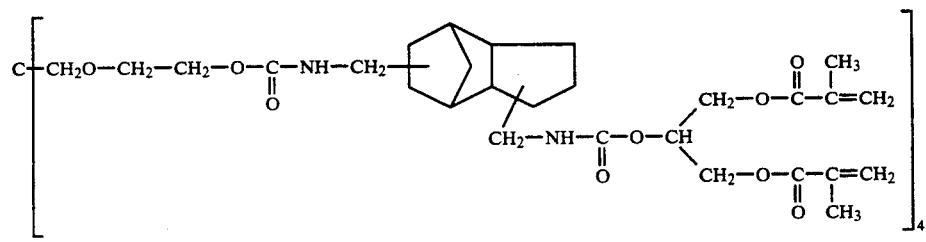
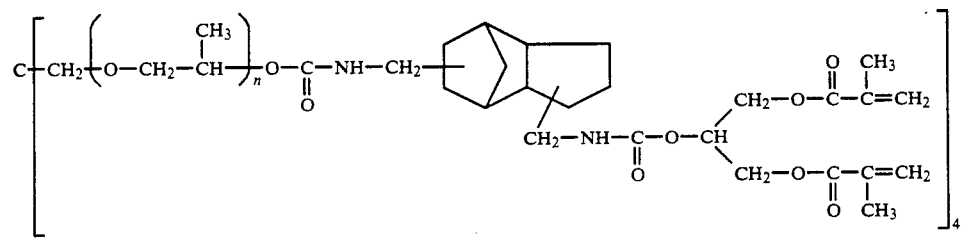
n = 1.225 (statistical mean for 4 chains)
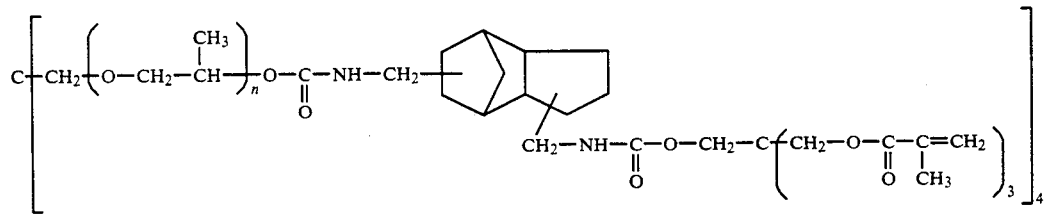
n = 1.225 (mean)
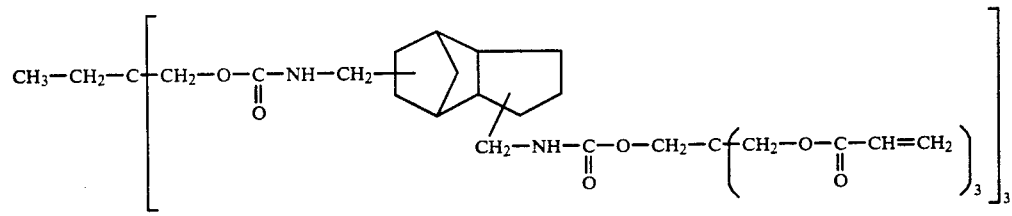
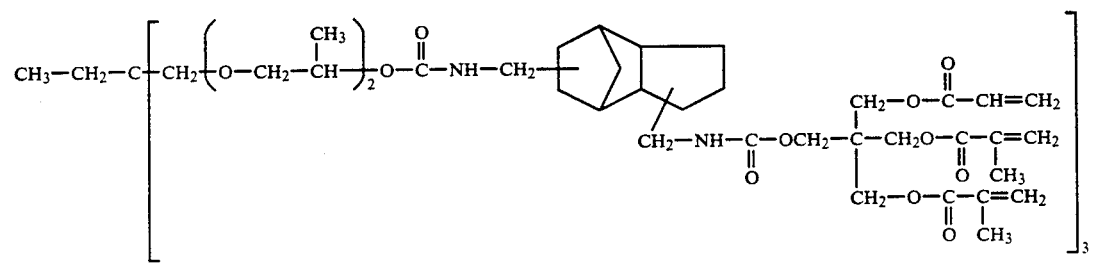

-continued
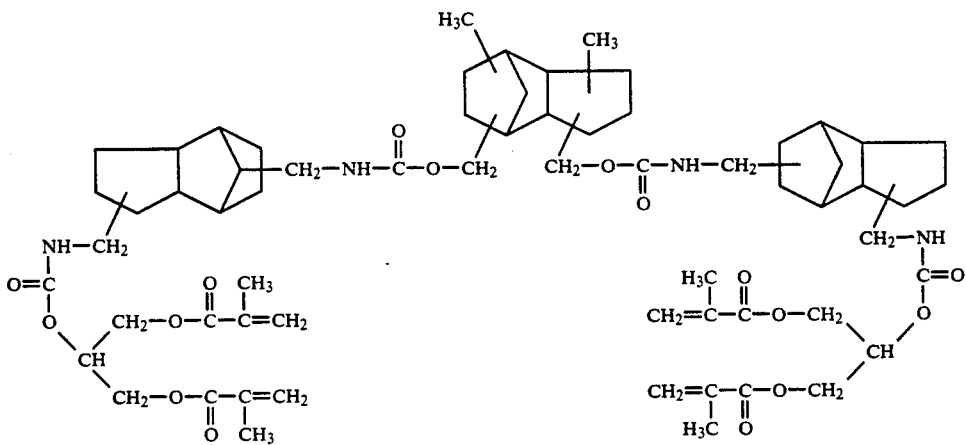
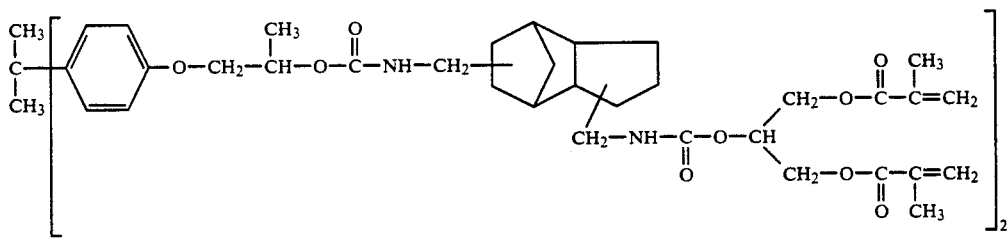
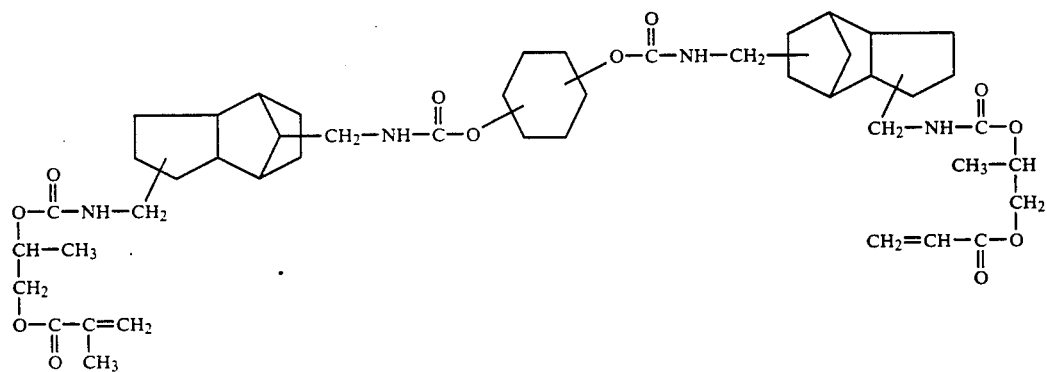
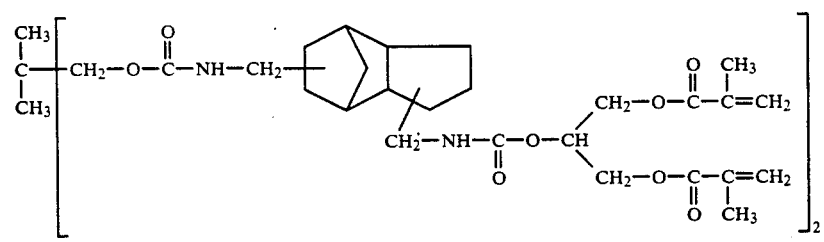
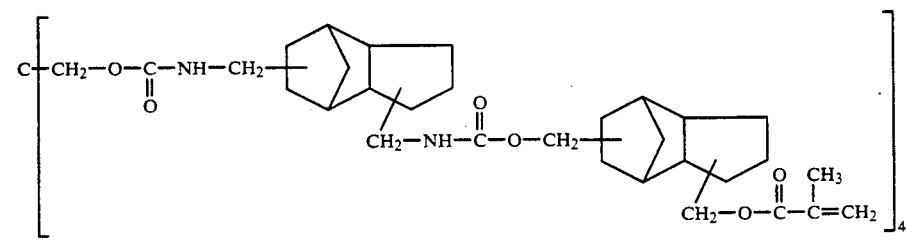

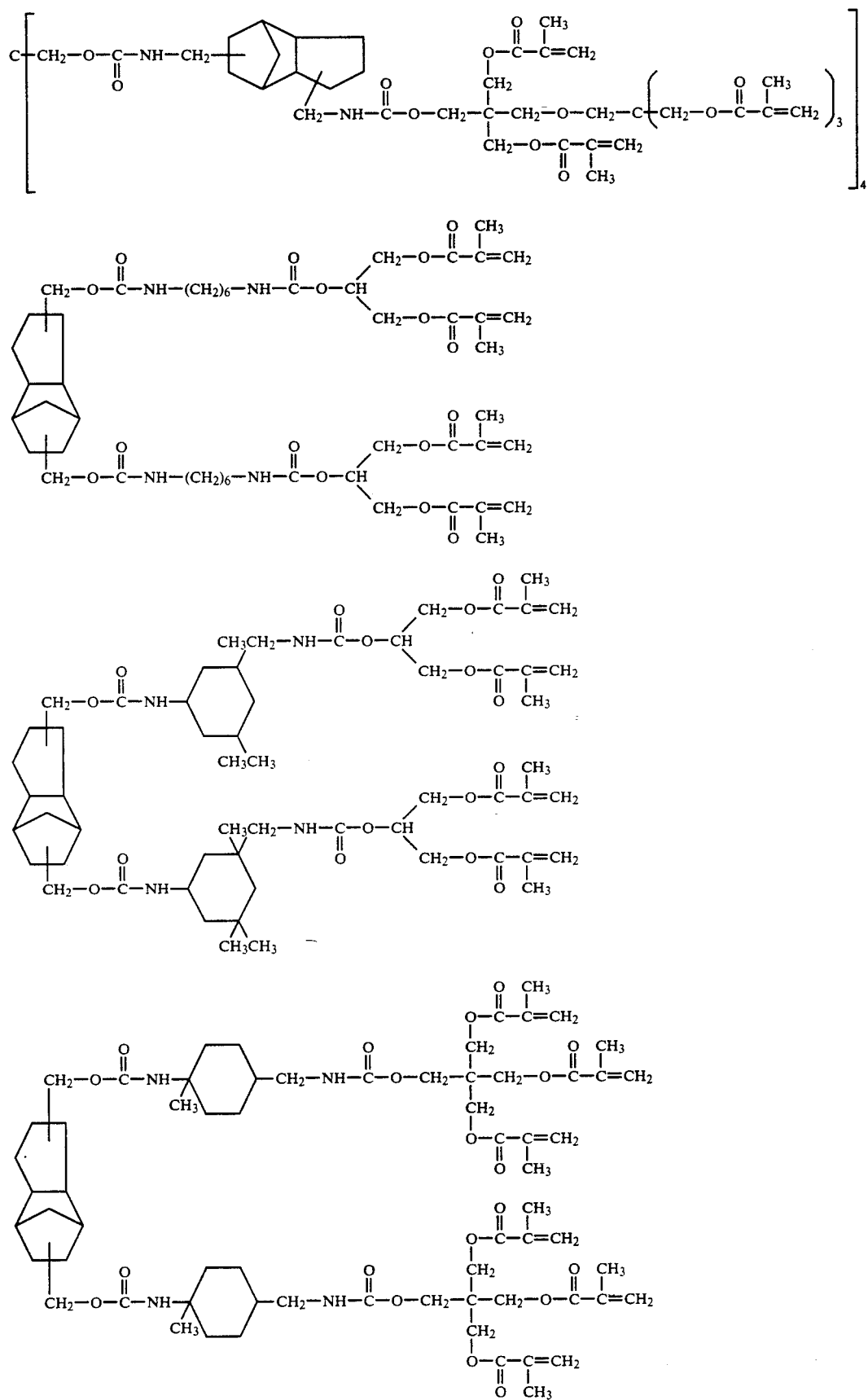

-continued

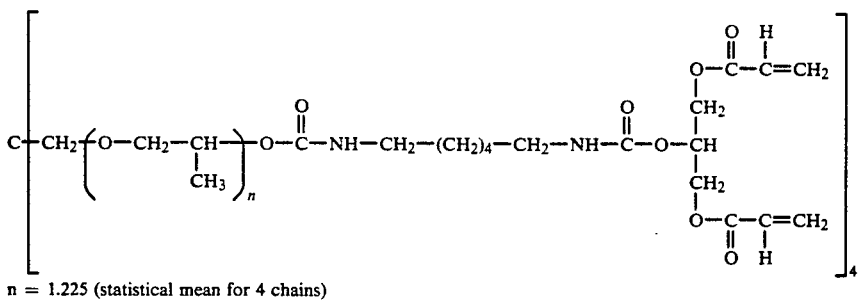

n = 1.225 (statistical mean for 4 chains)

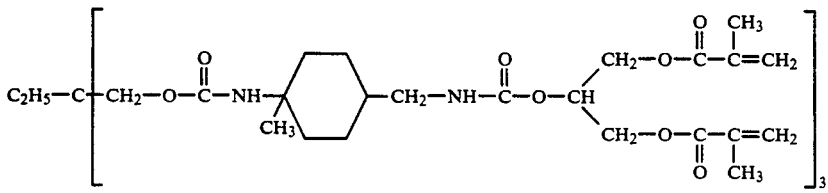

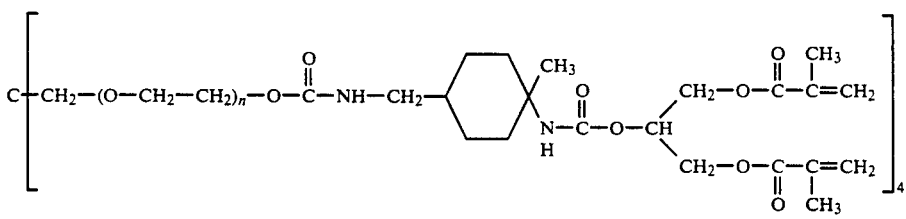

n = 1.225 (statistical mean for 4 chains)

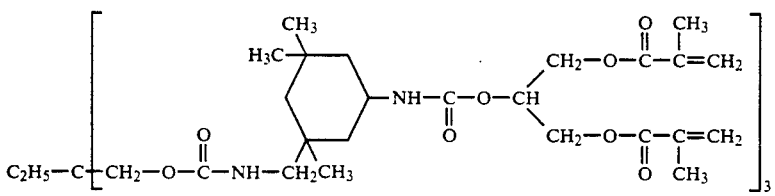

The so-called bis-GMA of the formula

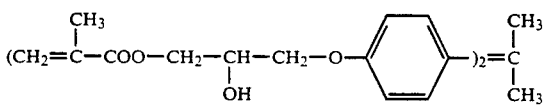

is particularly preferred as a monomer.

Of course, it is possible to employ mixtures of the various (meth)acrylic acid esters which can form cross-linkages. Mixtures of 20 to 70 parts by weight of bis-GMA and 30 to 80 parts by weight of triethylene glycol dimethacrylate may be mentioned as examples.

The preparations according to the invention in general contain 5 to 80 parts by weight, preferably 10 to 60 parts by weight, of carboxyl compounds, relative to the carboxamide group-containing (meth)acrylic acid esters.

The compositions according to the invention may contain fillers as further component. Fine powders which have a particle diameter in the range from 0.1 to 100 μm (if appropriate also in a polydisperse distribution) are preferred as fillers. Fillers may be fillers customary in the dental field (R. S. Baratz, J. Biomat. Applications, Vol 1, 1987. p 316 et seq.) such as inorganic glasses, silica, alumina or quartz powder.

As a result of a proportion of fillers in the preparations according to the invention, adhesive cements result which are particularly suitable for attaching bridges, crowns and other facing materials.

The proportion of the filler is in general 20 to 80 parts by weight, preferably 40 to 70 parts by weight, relative to the total preparation.

The adhesive components according to this invention may furthermore contain up to 10 parts by weight of customary additives such as stabilisers, inhibitors, light screens, colourants, pigments or fluorescent substances.

The preparations according to the invention can be prepared by mixing the carboxamide group-containing (meth)acrylic acid ester and the initiator and, if appropriate, the other components by vigorous stirring.

The preparations may also be solvent-free

The preparations according to the invention can be used as adhesive component for the treatment of collagen-containing materials.

In a particular embodiment, the collagen-containing material is conditioned before the treatment with the preparation according to the invention using a liquid having a pH value in the range from 0.1 to 3.5.

This liquid in general contains acids having a $pK_a$ value of less than 5 and, if appropriate, an amphoteric amino compound having a $pK_a$ value in the range from 9.0 to 10.6 and a $pK_B$ value in the range from 11.5 to 12.5. The conditioning liquid may contain, for example, the following acids:

phosphoric acid, nitric acid, pyruvic acid, citric acid, oxalic acid, ethylenediaminetetraacetic acid, acetic acid, tartaric acid, malic acid and maleic acid.

Amphoteric amino compounds which may be mentioned are preferably compounds of the formula

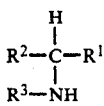

in which
R[1] represents a carboxyl group,
R[2] denotes hydrogen or a lower alkyl radical optionally substituted by hydroxyl, thio, methylthio, carboxyl, amino, phenyl, hydroxy-phenyl or the groups

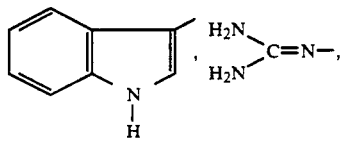

R[3] denotes hydrogen or phenyl,
where the radicals R[1] and R[3] can be linked via a propylene radical, or
in which
R[1] represents hydrogen,
R[2] represents the group

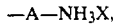

in which
A represents a doubly bonded alkylene radical having 1 to 6 carbon atoms and
X represents halogen, and
R[3] denotes hydrogen The following amphoteric amino compounds may be mentioned as examples: glycine, serine, threonine, cysteine, tyrosine, asparagine, glutamine, alanine, valine, leucine, isoleucine, proline, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochloride, butylenediamine hydrobromide, leucine hydrochloride and histidine hydrochloride.

The conditioning liquid may furthermore contain substances from the group comprising the polyethylene glycols and metal hydroxides. In particular, the above-mentioned polybasic acids can also be employed partly as metal salts as long as free acid functions remain.

Conditioning liquids which contain at least one of the acids from the group comprising pyruvic acid, ethylenediaminetetraacetic acid and citric acid and, if appropriate, an amphoteric amino compound from the group comprising glycine, N-phenylglycine and proline, are particularly preferred.

The application of the preparations according to the invention can be carried out, for example, as follows: In a dental repair, for example, after a mechanical cleaning of the collagen-containing dental material, the conditioning fluid is first applied using some cotton wool and allowed to act for a short time (for example 60 seconds), and the dental material is rinsed with water and dried in a stream of air. The preparation according to the invention is then applied in a thin layer, for example using a small brush, and dried in a stream of air. After the treatment according to the invention, the actual filling material, for example plastic filling materials customary in the dental field (K. Eichner, "Zahnärztliche Werkstoffe und ihre Verarbeitung" (Dental materials and their processing), Vol. 2, p. 135 et seq, Hüthig Verlag, 5th Edition 1985) is applied.

In a similar fashion, the preparations according to the invention can be used for attaching crowns, bridges and similar aids.

EXAMPLE 1

Synthesis of the New Carboxamide Group-Containing (Meth)acrylic Acid Esters (I)

1a) 3-acetamidopropyl methacrylate

Preliminary step:

290.3 g (4.00 mol) of methyl acetate were added dropwise with stirring at 25° C. to 300.4 g (4.00 mol) of 3-aminopropanol in 600 ml of methanol and the mixture was then heated to reflux for 5 hours. After concentrating the mixture, 328.0 g (70% of theory) of N-(3-hydroxypropyl)-acetamide were obtained by destillation at 0.3 mm Hg and 137°–140° C. in the form of a colorless liquid.

Subsequent step:

184.0 g (1.76 mol) of methacryloyl chloride were added dropwise in the course of 2 hours to an initial mixture, cooled to $-72°$ C., consisting of 206.2 g (1.76 mol) of N-(3-hydroxypropyl)-acetamide, 750 ml of methylene chloride, 228 g (2.25 mol) of triethylamine and 250 mg of 2,6-di-tert.butyl-4-methylphenol. The mixture was stirred for a further 2 hours at $-52°$ C. and the precipitated pale precipitate was then filtered off with suction at 0° C. The filtrate was subjected to aqueous work-up and the product was dried and, after concentrating on a rotary evaporator, distilled first at 100° C., and then the residue at 130° C. (in each case 0.1 mm Hg). 174.1 g (53% of theory) of 3- acetamidopropyl methacrylate were obtained in the form of a colorless oil.

IR (film) $\nu=3280, 2930, 1712, 1640, 1542, 1439, 1365, 1320, 1295, 1160, 938, 810$ cm$^{-1}$ $^1$H-NMR (CDCl$_3$, 200 MHz): $\delta=1.90$ (m, 2H, C—CH$_2$—C), 1.95 (bs, 3H, COCH$_3$), 1.99 (bs, 3H, vinyl.—CH$_3$), 3.33 (m, 2H, NCH$_2$), 4.24 (t, J=6 Hz, 2H, OCH$_2$), 5.60, 6.12 (2bs, each 1H, vinyl.-H), 5.95 (bs, 1H, NH)ppm.

MS (70 eV): m/z=185 (M+), 99 (M—C$_3$H$_5$CO$_2$H), 69 (C$_3$H$_5$CO+), 57 (C$_3$H$_5$O+), 43 (CONH+), 41 (C$_3$H$_5$+), 30.

Other (meth)acrylic acid esters (I) according to the invention can be prepared correspondingly. As an example of a propionamide according to the invention, 3-propionamidopropyl methacrylate having the following spectroscopic data may be mentioned:

IR (film): $\nu=3280, 3060, 2940, 2940, 1720, 1640, 1540, 1480, 1318, 1296, 1160, 1044, 932, 807$ cm$^{-1}$.

$^1$H-NMR (CDCl$_3$, 200 MHz): $\delta=1.18$ (t, J=7.5 Hz, 3H, CH$_2$CH$_3$), 1.89 (m, 2H, CH$_2$CH$_2$CH$_2$), 1.96 (bs, 3H, COCCH$_3$), 2.23 (q, J=7.5 Hz, 2H, CH$_2$CH$_3$), 3.34 (m, 2H, NCH$_2$), 4.22 (t, J=6.2 Hz, 2H, OCH$_2$), 5.6, 6.1 (2 bs, each 1H, vinyl.-H), 6.19 (bs, 1H, NH) ppm.

1b) N-3-Methacryloyloxypropylmethacrylamide 205.0 g (2.00 mol) of methacryloyl chloride were added dropwise with stirring at $-35°$ C. to an initial mixture of 75.1 g (1.00 mol) of 3-aminopropanol, 404.4 g (4.00 mol) of triethylamine and 100 mg of 2,6-di-tert-.butyl-4-methylphenol in 400 ml of methylene chloride and the mixture was kept at −30° C. for two hours. After filtering off the resultant precipitate with suction and aqueous extraction, the organic phase was concentrated to give 122.3 g (58% of theory) of product which, after eluting with ether/n-hexane (6:4) from a silica gel column, was present as a colorless oil.

IR (film): $\nu$=3340, 3080, 2970, 1723, 1663, 1623, 1539, 1456, 1321, 1300, 1168, 1010, 940, 816 cm$^{-1}$.

$^1$H-NMR (CDCl$_3$, 360 MHz): $\delta$=1.94 (m, 2H, CH$_2$CH$_2$CH$_2$), 1.98, 2.00 (2s, each 3H, CH$_3$), 3.41 (m, 2H, NCH$_2$), 4.26 (t, J=6.5 Hz, 2H, OCH$_2$), 5.35, 5.60, 5.72, 6.13 (4 bs, each 1H, vinyl.-H), 6.33 (bs, 1H, NH) ppm.

MS (70 eV): m/z=211 (M+), 142 (M—C$_3$H$_5$CO), 69 (C$_3$H$_5$CO+), 41 (C$_3$H$_5$+).

EXAMPLES 2 to 9

Production of the Preparations (II)

The adhesives according to the invention are produced by intensive mixing of the constituents shown in the following examples.

EXAMPLE 2

54 g water
46 g 2-acetamidoethyl methacrylate
138 mg camphor quinone

EXAMPLE 3

39 g water
41 g 2-acetamidoethyl methacrylate
20 g 25% by weight of aqueous glutaraldehyde solution
123 mg camphor quinone

EXAMPLE 4

52 g water
48 g 3-acetamidopropyl methacrylate
144 mg camphor quinone
48 mg propionaldehyde

EXAMPLE 5

40 g water
44 g 3-acetamidopropyl methacrylate
16 g 25% by weight of aqueous glutaraldehyde solution
132 mg camphor quinone

EXAMPLE 6

52 g water
48 g 3-propionamidopropyl methacrylate
144 mg camphor quinone

EXAMPLE 7

37 g water
43 g 3-propionamidopropyl methacrylate
20 g 25% by weight of aqueous glutaraldehyde solution
129 mg camphor quinone

EXAMPLE 8

33 g water
34 g N-3-methacryloyloxypropyl methacrylamide
102 mg camphor quinone

COMPARISON EXAMPLE 9

54 g water
46 g 5-propionamidopentyl methacrylate
138 mg camphor quinone

EXAMPLE 10: (USE)

The suitability of the adhesives (II) corresponding to Examples 1 to 9 is tested by determining the bonding strength of the light-activated plastic filling material based on multi-functional methacrylic acid esters and barium aluminosilicate Lumifor ® on dentine which has been pretreated successively with the conditioning liquid (consisting of 81.2 g water, 1.7 g sodium hydroxide and 17 g disodium ethylenediaminetetraacetate dihydrate: 60 seconds action, rinsing with water, air drying), the adhesive (60 seconds action, air drying) and a sealant based on polyfunctional methacrylic acid esters (Bayer Resin L ®) (applying and distributing thinly in a stream of air).

Extracted human teeth kept in the moist state are used for the test. The teeth are embedded by casting in epoxy resin; a smooth dentine surface is produced by subsequent grinding. The subsequent grinding is carried out using carbon paper 1000.

In order to prepare a test specimen for measuring the bonding strength, a cylindrical split Teflon mold is clamped onto the dentine surface treated as described above (Scand. J. Dent. Res. 88, 348-351 (1980)). A commercial plastic filling material is poured in as filling material. A no. 016 round drill clamped into a hole in a drill holding is attached to the Teflon mold and pressed from above into the material layer which is still in the process of hardening.

The entire arrangement is allowed to stand undisturbed at room temperature (25° C.) for 10 minutes, after which the drill holder and the Teflon mold are removed and the sample deposited under water at a temperature of 23° C. After 15 minutes, the sample containing the drill is mounted in an Instron tensile test apparatus (Scand. J. Dent. Res. 88, 348-351 (1980)); a tensile strength measurement is carried out at a velocity of 1 mm/min. The tensile strength is calculated by dividing the load applied on fracture of the filling by the cross-sectional area in the fracture surface of the test specimen. 5 measurements on test specimens were carried out in each case.

The results are summarized in the following table:

| Preparation according to Example No. | Tensile bonding strength [N/mm$^2$] |
|---|---|
| 2 | 19 ± 2 |
| 3 | 21 ± 3 |
| 4 | 14 ± 2 |
| 5 | 18 ± 3 |
| 6 | 8 ± 2 |
| 7 | 12 ± 4 |
| 8 | 6 ± 2 |
| 9 | 2 ± 1 |

It will be appreciated that the instant specification and claims are set forth by way of illustration and not limitation, and that various modifications and changes may be made without departing from the spirit and scope of the present invention.

What is claimed is:

1. A method of using an adhesive to adhere a substance to a collagen-containing material selected from the group consisting of tooth and bone, wherein said adhesive comprising carboxamide group-containing (meth) acrylic acid ester of the formula in which

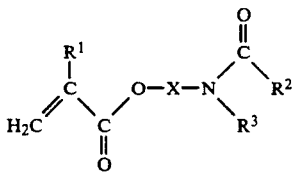

$R^1$ denotes hydrogen or methyl, $R^2$ denotes alkyl ($C_1$-$C_4$) or alkenyl ($C_2$-$C_4$), optionally substituted by hydroxyl, carboxyl, halogen or amino of the formula

in which $R^4$ and $R^5$ are identical or different and denote hydrogen or lower alkyl, $R^3$ denotes hydrogen or has one of the abovementioned meanings of $R^2$ and X is a divalent aliphatic ($C_1$-$C_6$) or cycloaliphatic radical ($C_3$-$C_6$), which can optionally contain one or more oxygen, sulphur and/or —$NR^4$-bridges, where $R^4$ has the abovementioned meaning, and which is optionally substituted by hydroxyl, carboxyl, halogen or amino of the formula

in which $R^4$ and $R^5$ have the abovementioned meaning, with the proviso that
 a) the sum of the carbon atoms in the radicals $R^2$, $R^3$ and X is not greater than six if these radicals contain no hetero-atoms, or
 b) the sum of the carbon atoms in the radicals $R^2$, $R^3$, $R^4$, $R^5$ and X is not greater than ten if at least one of these radicals contains at least one hetero atom.

2. The method according to claim 1, wherein the collagen-containing material is a tooth and the substance to be adhered to the tooth is a dental filling.

3. The method according to claim 1, wherein the collagen-containing material is bone.

4. The method according to claim 1, wherein the adhesive additionally contains an initiator.

5. The method according to claim 4, wherein the initiator comprises a mono- or dicarbonyl compound as a free radical former.

6. The method according to claim 1, in which
 $R^2$ denotes alkyl ($C_1$-$C_3$) optionally substituted by hydroxyl, carboxyl, fluorine, chlorine or amino,
 $R^3$ denotes hydrogen or has one of the abovementioned meanings for $R^2$ and
 X denotes a divalent aliphatic ($C_1$-$C_6$) and/or cycloaliphatic ($C_3$-$C_6$) radical, which is optionally substituted by hydroxyl, carboxyl, fluorine, chlorine or amino and can optionally contain one to five oxygen or —$NR_4$- bridges.

7. The method according to claim 1, wherein the carboxamide is dissolved in a solvent.

8. The method according to claim 1, wherein the adhesive additionally contains a coactivator.

9. The method according to claim 1, wherein the adhesive additionally contains a carbonyl compound.

10. The method according to claim 1, wherein the adhesive contains a (meth)acrylic acid ester capable of forming cross-linkages.

11. The method according to claim 1, wherein the adhesive additionally contains a filler.

* * * * *